United States Patent [19]

Altobelli et al.

[11] Patent Number: 5,110,318

[45] Date of Patent: May 5, 1992

[54] COMPOSITION AND METHOD FOR COLORING AND CONDITIONING HAIR

[76] Inventors: Rocco F. Altobelli, 1300 Deerwood Dr., Eagan, Minn. 55123; Wallace R. Hlavic, 3401 E. Calhoun Pkwy., Minneapolis, Minn. 55408; Annette Angell-Schram, 5108-192nd St., Farmington, Minn. 55024

[21] Appl. No.: 493,303

[22] Filed: Mar. 14, 1990

Related U.S. Application Data

[60] Continuation-in-part of Ser. No. 408,604, Sep. 18, 1989, Pat. No. 5,002,076, which is a division of Ser. No. 178,320, Apr. 6, 1988, Pat. No. 4,913,898.

[51] Int. Cl.$^5$ .............................................. A61K 7/13
[52] U.S. Cl. ............................................. 8/405; 8/406; 8/407; 8/408; 8/410; 8/411; 8/414; 8/415; 8/435; 424/70
[58] Field of Search ................ 8/405, 406, 407, 408, 8/414, 415, 410, 411, 425, 426, 428, 429, 435; 424/70; 252/DIG. 10

[56] References Cited

U.S. PATENT DOCUMENTS

| | | | |
|---|---|---|---|
| 3,642,423 | 2/1972 | Bil et al. | 8/414 |
| 3,884,627 | 5/1975 | Brody et al. | 8/410 |
| 3,950,127 | 4/1976 | Halasz et al. | 8/414 |
| 3,951,589 | 4/1976 | Alperin et al. | 8/415 |
| 3,973,900 | 8/1976 | Husemeyer et al. | 8/415 |
| 4,021,486 | 5/1977 | Halasz et al. | 8/415 |
| 4,092,102 | 5/1978 | Halasz et al. | 8/411 |
| 4,566,876 | 1/1986 | Brown et al. | 8/411 |
| 4,678,475 | 7/1987 | Hoshowski et al. | 8/405 |
| 4,689,217 | 8/1987 | Restaino et al. | 8/405 |
| 4,690,817 | 9/1987 | Davis et al. | 8/405 |
| 4,727,192 | 2/1988 | Junino et al. | 8/415 |
| 4,749,379 | 6/1988 | Junino et al. | 8/408 |
| 4,838,894 | 6/1989 | Kijek et al. | 8/412 |

*Primary Examiner*—A. Lionel Clingman
*Assistant Examiner*—William S. Parks
*Attorney, Agent, or Firm*—Merchant, Gould, Smith, Edell, Welter & Schmidt

[57] ABSTRACT

A method for non-permanently or semi-permanently coloring hair with an aqueous clay-based composition that involves applying the composition to hair and exposing the hair to heat for a period of time sufficient to dry the composition to a hard and flaky state. The hair coloring composition also can include effective amounts of a reconstruction component (protein), a moisturizer component having sodium hyaluronate, and a shine imparting component having henna extract.

34 Claims, No Drawings

COMPOSITION AND METHOD FOR COLORING AND CONDITIONING HAIR

CROSS-REFERENCE TO RELATED APPLICATIONS

This application is a continuation-in-part of U.S. Pat. application Ser. No. 408,604, filed Sep. 18, 1989, now Pat. No. 5,002,076, which in turn is a divisional application of U.S. Pat. application Ser. No. 178,320, filed Apr. 6, 1988, now Pat. No. 4,913,898.

FIELD OF THE INVENTION

This invention relates to aqueous clay-based hair treatment compositions including a reconstruction component, a shine imparting component and a moisturizing component that can be used in a single application to condition hair. The invention also relates to single application, aqueous clay-based hair coloring compositions incorporating non-permanent or semi-permanent agents for coloring hair, as well as reconstruction, shine imparting and moisturizing components for conditioning hair.

BACKGROUND OF THE INVENTION

A variety of chemical preparations are available and commonly used to change the natural characteristics of hair. Color and style are typically changed using dyes, bleaches and permanent-waving preparations. For example, hair color may be non-permanently (i.e. temporarily), semi-permanently or permanently changed depending on the particular coloring compositions employed. These chemical preparations can damage hair.

In general, hair has a filamentous structure with an inner component referred to as the cortex and an outer flap-like component referred to as the cuticle. In the natural state, the cuticle is closed providing natural elasticity. When the cuticle is open, this natural elasticity is lost. Hair damaged by chemical preparations, in many cases, exhibits open cuticles. For example, use of dye mixtures can dry hair resulting in a loss of elasticity and body.

To restore desired elasticity and body to hair following use of chemical preparations, hair conditioning treatments are commonly employed. Typical hair conditioning treatments involve the use of a number of components to restore hair qualities lost during chemical treatment. To reconstruct the hair and bring back elasticity a protein pack is commonly employed. Also, a component such as henna can be applied to the hair to impart shine or luster. Another typical post-treatment conditioning component is a moisturizer which is used to enhance the body of hair.

While hair treatments that reconstruct, add shine, and moisturize hair are known, these treatments are both time consuming and labor intensive. Specifically, each component in the hair conditioning process must be separately applied and removed. The application of a protein pack typically requires 10 to 20 minutes and must then be removed prior to applying further conditioning components. Treatment of hair with a shine imparting component such as henna can involve up to one hour. The shine imparting component must also be removed before another conditioning preparation, such as a moisturizer is used. In the case of a three part hair conditioning treatment, to reconstruct, impart shine and moisturize hair, separate application and removal of each component requires a total treatment time of about 1 to 1½ hours. It is to be understood that this 1 to 1½ hour process is in addition to whatever time is involved in the particular dye or permanent-waving treatment which precedes the hair conditioning procedure. For example, non-permanent or semi-permanent coloring of hair, which typically requires 5 to 30 minutes of application, in conjunction with hair conditioning could require a total treatment time of about 1 to 2 hours.

Accordingly, a substantial need exists for a hair conditioning composition containing a reconstruction component, a shine imparting component and a moisturizing component that can be employed in a single application procedure of short duration. A substantial need also exits for a single application composition for coloring hair, which in addition to non-permanent or semi-permanent coloring agents, contains reconstructive, shine imparting and moisturizing components for conditioning hair.

SUMMARY OF THE INVENTION

The present invention provides a hair treatment composition in the form of an aqueous clay-based paste which includes effective amounts of a reconstruction component, a shine imparting component and a moisturizing component. It has been found that the composition is useful in a method to condition hair involving: applying the preparation to hair; and exposing the prepared hair to heat until the preparation dries to a hard flaky state. The dried pack is then solubilized and removed with a commercially available cleansing shampoo.

The present invention also provides a hair coloring composition in the form of an aqueous clay-based paste which includes effective amounts of non-permanent or semi-permanent coloring agents for coloring hair, as well as effective amounts of reconstructive, shine imparting and moisturizing components for conditioning hair. As with the conditioning composition described above, the coloring composition is applied to the hair, exposed to heat until dry and then removed with a commercially available shampoo. In this instance, non-permanent hair coloring agents are defined as those coloring preparations which give a color that is completely removable in one shampoo, while semi-permanent coloring agents are defined as those which will last through at least four or more washings of the hair.

In a preferred embodiment, the method of use of the hair treatment composition involves a two step heat treatment. In the first step, the prepared hair is enclosed in a cover means such as a cap. In the second heat step, which is of shorter duration than the first, the prepared hair is uncovered and exposed directly to the heat.

In a second preferred embodiment, the method of use of the hair coloring composition of the present invention involves a three step process, including a two step heat treatment. In the first step, the hair prepared with the composition is enclosed in a cover means such as a cap, and is exposed to heat for a predetermined duration. In the second step, which is shorter in duration than the first step, the prepared hair is uncovered and exposed directly to the heat treatment. In the third, and final step, the dried hair coloring composition is washed from the hair using a commercially available cleansing shampoo, to yield non-permanently or semi-permanently colored and conditioned hair. In addition, the method of use of the present invention may employ a single heat treatment step, wherein the hair coated with the composition is directly exposed to heat treatment until it dries upon the hair. In this instance, a diminished, and therefore, more subtle, coloring effect is imparted to the hair when compared to the two-step heat treatment described above.

The hair treatment composition and method of use of the present invention exhibits a number of advantages. First, the present invention eliminates the need for multiple step conditioning treatments which involve separate application and removal of conditioning components. The present invention provides a composition that can be used in a single application to condition hair by reconstructing damaged hair together with adding shine and body. Second, in contrast to the existing multiple step conditioning treatments, which may require from about 1 hour to 1½ hours, the method of the present requires only about 20 to 40 minutes. Third, the present invention is labor saving in that one application step is required, thereby enabling more efficient use of beauty salon personnel.

The moisturizer hyaluronic acid penetrates deeply; while clay locks in moisture and protein, naturally sealing the cuticle layer. The present composition conditions, seals and enhances natural sheen and a light but full appearance on hair.

The hair coloring compositions and method of the present invention provides the advantages of a one-step non-permanent or semi-permanent coloring and conditioning treatment. Accordingly, as with the above-described conditioning composition, the coloring composition of the present invention saves time and labor allocation. Thus, in contrast to a multiple-step coloring and conditioning process requiring 1 to 2 hours, the method and compositions of the present invention can accomplish the same result with a one-step process requiring 20 to 40 minutes.

DETAILED DESCRIPTION OF THE INVENTION

The present hair conditioning compositions as preferably formulated include a sufficient amount of a clay component to form a malleable paste having an oil phase and water, together with effective amounts of a reconstruction component, a shine imparting component and a moisturizing component. The desired paste consistency of the composition is achieved and maintained with the aid of cationic, nonionic and anionic polymers, surfactants and emulsifiers.

The present paste is an aqueous clay-based composition. Aqueous clay-based composition refers to a paste incorporating water and clay in amounts sufficient to form a dry and flaky coating on hair when subjected to heat as described herein. Preferably, the paste has the consistency of a light modeling clay. In a preferred embodiment, from about 15-25% of the composition is clay (this percentage and all following percents being weight percents relative to the total weight of the composition). In general, clay refers to a composition of extremely fine crystals or particles of rock which in many cases has the characteristic of plasticity. The very fine particles yield a very large specific surface that is physically sorptive and chemically surface-reactive.

The present compositions can employ a number of clays either alone or in combination. For example, kaolin, fuller's earth, montmorillonite, georgia or calcine clays can be used. Preferred compositions employ a combination of kaolin and fuller's earth. More preferably, the clay of the present composition is from about 13-20% kaolin available from Georgian Kaolin as Hydride Flat D and about 2-12% fuller's earth. While the combination of kaolin and fuller's earth is preferred, one of skill in the art will be able to use other types of clays based on an evaluation of the hydration, emulsion lattice filling characteristics, and thixotropic and rheologic properties of the preferred compositions described herein.

The present paste will incorporate an effective amount of reconstruction component in the form of protein. Preferably, the composition will include from about 2-20% substantive protein. Most preferably, the composition will include at least 10% protein having average molecular weights ranging from 1,000 to 5,000. Preferred sources of protein include hydrolyzed animal protein such as available from Inolex as Lexein X250 and cocodimonium hydrolyzed animal protein available from Croda as Croquat M. Other protein sources that can be used include oat flour available from Quaker Oats as Oat Pro or Stero Pro.

The present composition can be used to deliver an amount of moisturizer to the hair effective to provide body without adding a weighty oil coat to the hair. The moisturizing component is preferably from about 0.1-5.0% of the composition. While the present composition may incorporate a number of common moisturizers such as Glycerin, Acetamide MEA or honey, the preferred moisturizer is hyaluronic acid (now known as sodium hyaluronate), available from Diagnostics as Hyalure TN. It is believed that hyaluronic acid penetrates deeply into the hair and can be used in very small amounts. The present composition utilizes from about 0.000001-1% hyaluronic acid. While hyaluronic acid functions as a natural moisturizer, it may also bind to and carry the protein in the composition through the cuticle to the cortex of the hair to aid in reconstruction of the hair.

The present composition also incorporates a shine or sheen imparting component. Useful shine imparting components include henna extract, PVM/MA Copolymer, available from GAF Corporation as Gantrez AN169, PPG-5 Lanolin in ether available from Amerchol as Solulan PB-5 and Amodiomethicone available from Dow Corning as a component of Dow Corning 929 Emulsion. These shine imparting components may be used alone or in combination as is known by those of skill in the art. Preferred compositions include from about 0.5-20% of the shine imparting component. Most preferably, the shine imparting component includes from about 5-15% henna extract and 0.5-5% PVM/MA copolymer.

The present composition includes an oil phase that serves as a lubricating vehicle to enhance application. Useful oil phase compounds include fatty alcohols. The preferred oil phase components are fatty alcohols such as stearyl alcohol, and cetyl alcohol. The oil phase in the present composition preferably ranges from about 2-10%. More preferably, the oil phase is from about 3-7% fatty alcohol.

The aqueous phase of the present composition is preferably from about 20-60% water. More preferably, from about 20-40% water and most preferably from about 20-30% water. To eliminate the presence of undesired mineral impurities, deionized water is most preferred.

Nonionic emulsifiers are commonly added to the present composition to enhance solubilization of oil soluble components and fragrance. Preferably a combination of cationic and nonionic emulsifiers is used. Useful nonionic emulsifiers include nonoxynol surfactants such as available from Minnesota Solvents as Surfonic N-95. Preferred cationic emulsifiers include tallowtrimonium chloride, available from Dow Corning 929 Emulsion, Quaternium 22, available from Van Dyke as Ceraphyl 60. In preferred compositions the cationic emulsifier component ranges from about 0.25-5%.

The present compositions can also include minor but effective amounts of various adjuvant materials including viscosity modifiers, preservatives and fragrances.

In the manufacture of the clay-based compositions, the above-described components are mixed together in phases and in order consistent with available manufacturing equipment until a light modeling clay consistency is achieved. In order to avoid loss of malleability, the composition must be rapidly transferred to a storage container, such as a jar, before the composition further sets or gels.

The present clay-based compositions for coloring hair as preferably formulated are prepared by the same methods and contain the same components as the conditioning compositions described above. However, the coloring compositions also contain effective amounts of non-permanent or semi-permanent coloring agents for coloring hair.

In contrast to the above-described conditioning compositions, the coloring compositions preferably contain from about 5-25% clay, and in a particularly preferred embodiment contain from about 2-12% kaolin and about 0.5-7% fuller's earth. The coloring compositions also preferably contain 2-20% protein with at least 5% of the protein having average molecular weights ranging from 1,000 to 5,000, henna extract as a shine imparting component from about 1-15%, and an aqueous phase from about 20-70%, and more preferably from about 50-70%. In addition, hyaluronic acid is provided from about 0.00001-1.0% in its salt form as sodium hyaluronate from Lifecore.

The coloring compositions deliver effective amounts of non-permanent or semi-permanent coloring agents to the hair, while retaining the benefits imparted to the hair by the reconstructive, shine imparting and moisturizing components described above. The non-permanent or semi-permanent coloring agents are provided from about 0.00001-5.0%, preferably from about 0.1-5.0%, and more preferably from about 0.5-5.0% of the composition.

The hair coloring compositions according to the present invention may incorporate any of a number of non-permanent and semi-permanent coloring agents such as FD&C (Food, Drug & Cosmetic), D&C (Drug & Cosmetic) and HC (Hair Color) dyes and their intermediates, including various pyrazolone, monoazo, xanthene, triphenylmethane and diazo compounds, metal-complex dyes, including azo complexes of cobalt or chromium and oxidation dye intermediates including nitrophenylenediamines such as o-nitro-p-phenylenediamine and p-nitro-o-phenylenediamine.

It will be appreciated that the clay-based coloring compositions of the present invention can incorporate any combination of the moisturizing, reconstructing and shine imparting components previously described. Thus, the coloring compositions may contain the coloring agents alone, or in combinations containing one, two or all three of the moisturizing, reconstructing and shine imparting components.

It will be further appreciated that strongly cationic components, such as dicetyl dimonium chloride can be incorporated into the clay-based coloring compositions of the present invention. However, care must be taken with the proportions of such components to be added, as an excess amount will complex with the anionic coloring components of the present invention, thereby reducing the effectiveness of the clay-based compositions to color hair.

In use the compositions of the present invention are preferably applied to hair after application of a chemical preparation such as a dye, bleach or permanent-waving preparation. In addition, the compositions for coloring hair are applied to the hair in a one-step coloring and conditioning process. Prior to application of the composition the hair is shampooed and excess water squeezed out. The composition is dispensed from its container and rubbed between the hands to enhance the liquidity and spreadability of the composition prior to application, thereby facilitating distribution of the composition in the hair. A liberal amount of the composition is applied to and worked into the hair and scalp. The treated hair is then exposed to heat for a period of time sufficient to dry the composition to a hard and flaky state. This is accomplished by exposing the hair to temperatures from about 80°-120° F. for a period of time between about 15-45 minutes.

Preferably, the treated hair is subjected to a two-step heat process. In the first step, the hair is enclosed in cover means such as a plastic cap or the like. The covered hair is heated for a period of time between about 13-30 minutes at a temperature from about 80°-120° F. under a preheated salon dryer of the type known in the art. Most preferably, the covered hair is heated for a period of time between about 20-30 minutes at a temperature of from about 90°-110° F. It is to be understood that by covering the hair with a cap the clay-based composition retains moisture for an extended period of time allowing the protein in the composition to bake into the hair thereby enhancing reconstruction of damaged hair. If hair dries too quickly, incorporation of protein into the hair is less complete. By covering the hair, protein incorporation is maximized.

The second step of the preferred heat treatment involves removing the cap and exposing the hair directly to heat at a temperature from about 80°-120° F. for a period of time between about 2-15 minutes. Most preferably, the second step of the heat treatment involves separating the hair with fingers and exposing the uncovered hair to a temperature of from about 90°-110° F. for a period of time between about 3-8 minutes. The head is then allowed to cool for several minutes. The application of heat to the exposed hair completes the drying of the composition, thereby polishing the hair and sealing the cuticle.

After the composition has dried to the desired hard and flaky state, it is removed by wetting the head with water and applying a cleansing shampoo of a type well known in the art.

The above-described method of use may also be employed with the hair coloring compositions of the present invention. Accordingly, as described above, the hair is first shampooed and the excess water is squeezed out. The clay-based composition, including the incorporated non-permanent dyeing agent, is applied and heat treated according to the above-described method. Finally, the clay-based coloring composition is removed by cleansing the hair with a shampoo of the type well known in the art.

In will be appreciated that the compositions for coloring hair according to the present invention can be optionally subjected to a one-step heat process. In this instance, the hair coated with the composition is directly exposed to a temperature from about 80°-120° F. for a period of time between 2-15 minutes. Most preferably, the heat treatment involves separating the hair with the fingers and exposing the uncovered hair to a temperature of from about 90°-110° F. for a period of time between 3-8 minutes. The hair is then allowed to cool for several minutes. When utilized in this manner, the coloring compositions according to the present invention impart a diminished, and therefore, more subtle, coloring effect to the hair being treated.

It will be further appreciated that the compositions for coloring hair according to the present invention may be utilized as a corrective coloring agents for eliminating unnatural color tones in previously dyed or treated hair. For example, hair which has been dyed to a brunette coloration frequently displays a red tone after the passage of time and/or exposure to the sun. By utilizing a slate-blue hair coloring composition according to the present invention, such red-toned hair can be returned to a natural brunette coloration, and at the same time, can be conditioned. In addition, it will be appreciated by those skilled in the art that the particular dye coloration employed in the clay-based coloring compositions of the present invention do not necessarily correspond to the coloration imparted to the hair. For example, utilization of certain green dyes will in fact impart a golden coloration to the hair to be dyed.

It will also be appreciated that both the clay-based conditioning and clay-based coloring and conditioning compositions according to the present invention can be utilized in either a beauty salon or at home. An individual may have the compositions of the present invention applied by a hair treatment professional at a beauty salon or shop, or may optionally purchase the present compositions at a salon or other appropriate retail outlet, and apply the compositions themself at home.

The present composition will be further described by reference to the following detailed Examples, and it is understood that the invention is not limited thereto. All parts are by weight unless otherwise indicated.

EXAMPLE 1

The constituents below are blended in the weight percentages indicated to yield a paste composition.

| CTFA Designation | Trade Name | % by Weight |
| --- | --- | --- |
| Deionized Water | Deionized Water | Q.S. to 100% |
| Kaolin | Hydride | 18.13 |
| Hydrolyzed Animal Protein | Lexein X250 | 10.00 |
| Henna Extract | Henna Extract | 10.00 |
| Amodimethicone (and) Nonoxynol-10 (and) Tallowtrimonium Chloride | Dow Corning 929 Emulsion | 8.00 |
| Stearyl Alcohol | Stearyl Alcohol | 2.52 |
| Fuller's Earth | Fuller's Earth | 4.41 |
| PVM/MA Copolymer | Gantrez AN169 | 5.00 |
| Glycerin | Glycerin | 3.00 |
| Magnesium Aluminum silicate | Veegum HV | 2.64 |
| Nonoxynol-10 | Surfonic N-95 | 0.25 |
| Oat Flour | Oat Pro | 1.72 |
| Acetamide MEA | Acetamide MEA | 1.50 |
| Quaternium-22 | Ceraphyl 60 | 0.25 |
| Sodium Hyaluronate | Sodium Hyaluronate | >0.01 |
| Cocodimonium Hydrolyzed Animal Protein | Croquat M | 0.25 |
| PPG-5 Lanolin Ether | Solulan PB-5 | 0.50 |
| Dimethyl Lauramine Oleate | Necon Lo | 1.50 |
| Honey | Honey | 0.25 |
| Cationic Collagen Polypeptides | Cationic Collagen Polypeptides | 2.00 |
| Cetearyl Alcohol (and) PEG-40 Castor Oil (and) Stearalkonium Chloride | Cycloton SCS | 3.19 |
| Cetyl Alcohol | Cetyl Alcohol | 0.21 |
| Glyceryl Stearate (and) PEG-100 Stearate | Arlacel 165 | 1.00 |
| Methylparaben | Methylparaben | 0.30 |
| Propylparaben | Propylparaben | 0.08 |
| DMDM Hydantoin | Glydant | 0.35 |
| Gluteral | Ucarcide 225 | 0.20 |
| Fragrance | Fragrance | Q.S |

The constituents below are blended in the weight percentages indicated to yield a paste composition which can temporarily alter the color of hair through the use of non-permanent or semi-permanent coloring compositions, as well as condition the treated hair.

EXAMPLE 2

The constituents listed below result in a lavender colored clay pack for coloring and conditioning white or grey hair.

| CTFA Designation | Trade Name | % by Weight |
| --- | --- | --- |
| Deionized Water | Deionized Water | Q.S. to 100% |
| Henna Extract | Henna Extract | 7.00 |
| Methylparaben | Methylparaben | 0.30 |
| Magnesium Aluminum Silicate | Veegum HV | 1.00 |
| Sodium Hyaluronate | Lifecore Sodium Hyaluronate | >0.01 |
| Glycerin | Glycerin | 0.35 |
| Honey | Honey Blend #3 | 0.10 |
| Acetamide MEA | Acetamide MEA | 0.01 |
| Oat Flour | Stero Pro | 1.34 |
| PVM/MA Copolymer | Gantrez AN 169 (sol.) | 4.00 |
| Quaternium-22 | Ceraphyl 60 | 0.01 |
| Hydrolyzed Animal Protein | Lexein 250 | 6.00 |
| Cationic Collagen Polypeptides | Cationic Collagen Polypeptides (Amerchol) | 1.50 |
| Cocodimonium Hydrolyzed Animal Protein | Croquat M | 1.50 |
| Panthenol DL | Panthenol | 0.50 |
| Stearyl Alcohol | Stearyl Alcohol | 0.01 |
| Cetyl Alcohol | Cetyl Alcohol | 4.09 |
| Glyceryl Stearate (and) PEG-100 Stearate | Arlacel 165 | 2.14 |
| Cetearyl Alcohol (and) PEG-40 Castor Oil (and) Stearalkonium Chloride | Cycloton SCS | 2.14 |
| Cetearyl Alcohol (And) Stearalkonium Chloride (and) Polysorbate 60 | Mazerwax 163 | 1.33 |
| Dimethyl Lauramine Oleate | Necon Lo | 2.01 |
| Dicetyldimonium Chloride | Adogen 432 CG | 0.50 |
| Propylparaben | Propylparaben | 0.10 |
| PPG-5 Lanolin Ether | Solulan PB-5 | 0.21 |
| Disperse Violet No. 1 | Disperse Violet No. 1 | 0.06 |
| D&C Violet No. 2 | D&C Violet No. 2 | 0.02 |
| External D&C Violet No. 2 | External D&C Violet No. 2 | 0.02 |
| Cyclomethicone | Dow Corning 345 | 0.25 |
| Dimethicone | Dow Corning 200 | 0.25 |
| Polymethoxy bicyclic Oxazolidine | Nuosept C | 0.50 |

| CTFA Designation | Trade Name | % by Weight |
| --- | --- | --- |
| Kaolin | Huber 35/Hydrite | 6.50 |
| Fullers Earth | Fullers Earth 100 | 2.70 |
| Amodimethicone (and) Nonoxynol-10 (and) Tallowtrimonium Chloride | Dow Corning 929 Emulsion | 3.00 |
| Nonoxynol-10 | Surfonic N-95 | 0.01 |
| Fragrance | Fragrance | Q.S. |

While the above example has been described with paticularity, it is to be understood that the dye loads incorporated into the clay-based compositions of the present invention can occur at anywhere between about 0.00001 to 5.00 percent by weight, depending upon the tone and intensity of coloration sought. In addition, the other listed components can occur within any range of values which render effective clay-based coloring and conditioning compositions in accordance with the present invention. For example, the water component can occur at anywhere between about 20-70% by weight, the clay components between about 5-25% by weight, the moisturizing components between about 0.10-5.00% by weight, the henna component between about 1-15% by weight, the protein components between about 2-20% by weight, the sodium hyaluronate between about 0.00001-1.00% by weight and the emulsifying components between about 0.25-10.00% by weight.

EXAMPLE 3

The constituents for Example 3 result in a light violet colored clay pack for coloring and conditioning blonde, white and grey hair. The constituents are the same as listed in Example 2, with the following variations:

| CTFA Designation | Trade Name | % by Weight |
| --- | --- | --- |
| Disperse Violet No. 1 | Disperse Violet No. 1 | 0.04 |
| D&C Violet No. 2 | D&C Violet No. 2 | 0.00 |
| External D&C Violet No. 2 | External D&C Violet No. 2 | 0.00 |
| Polymethoxy Bicyclic Oxazolidine | Nuosept C | 0.00 |
| Gluteral | Ucarcide 225 | 0.15 |
| DMDM Hydantoin | Glydant | 0.35 |

EXAMPLE 4

The constituents for Example 4 result in an opaque lavender colored clay pack for coloring and conditioning white or grey hair. The constituents are the same as listed in Example 2, with the following variations:

| CTFA Designation | Trade Name | % by Weight |
| --- | --- | --- |
| Disperse Violet No. 1 | Disperse Violet No. 1 | 0.04 |
| D&C Violet No. 2 | D&C Violet No. 2 | 0.00 |
| External D&C Violet No. 2 | External D&C Violet No. 2 | 0.00 |

EXAMPLE 5

The constituents for Example 5 result in a opaque lavender colored clay pack for coloring and conditioning white or grey hair. The constituents are the same as listed in Example 2, with the following variations:

| CTFA Designation | Trade Name | % by Weight |
| --- | --- | --- |
| Disperse Violet No. 1 | Disperse Violet No. 1 | 0.03 |
| D&C Violet No. 2 | D&C Violet No. 2 | 0.00 |
| External D&C Violet No. 2 | External D&C Violet No. 2 | 0.00 |

EXAMPLE 6

The constituents for Example 6 result in an opaque lavender colored clay pack for coloring and conditioning blonde hair. The constituents are the same as listed in Example 2, with the following variations:

| CTFA Designation | Trade Name | % by Weight |
| --- | --- | --- |
| Henna Extract | Henna Extract | 2.00 |
| Disperse Violet No. 1 | Disperse Violet No. 1 | 0.02 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 7

The constituents for Example 7 result in an opaque lavender colored clay pack for coloring and conditioning blonde hair. The constituents are the same as listed in Example 2, with the following variations:

| CTFA Designation | Trade Name | % by Weight |
| --- | --- | --- |
| Henna Extract | Henna Extract | 2.00 |
| Disperse Violet No. 1 | Disperse Violet No. 1 | 0.01 |
| HC Blue No. 2 | HC Blue No. 2 | 0.03 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 8

The constituents for Example 8 result in a golden wheat colored clay pack for coloring and conditioning blonde hair. The constituents are the same as listed in Example 2, with the following variations:

| CTFA Designation | Trade Name | % by Weight |
| --- | --- | --- |
| Henna Extract | Henna Extract | 2.00 |
| Intersperse Pink B2 | Intersperse Pink B2 | 0.06 |
| HC Black No. 9 | HC Black No. 9 | 0.08 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 9

The constituents for Example 9 result in a golden wheat colored clay pack for coloring and conditioning blonde hair. The constituents are the same as listed in Example 2, with the following variations:

| CTFA Designation | Trade Name | % by Weight |
| --- | --- | --- |
| Henna Extract | Henna Extract | 2.00 |
| Intersperse Pink B2 | Intersperse Pink B2 | 0.12 |
| HC Black No. 9 | HC Black No. 9 | 0.16 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 10

The constituents for Example 10 result in a blue colored clay pack for coloring and conditioning brunette hair. The constituents are the same as listed in Example 2, with the following variations:

| CTFA Designation | Trade Name | % by Weight |
| --- | --- | --- |
| Henna Extract | Henna Extract | 2.00 |
| HC Blue No. 1 | HC Blue No. 1 | 0.08 |
| HC Blue No. 2 | HC Blue No. 2 | 0.62 |
| o-nitro-p-phenylenediamine | o-nitro-p-phenylenediamine | 0.01 |
| p-nitro-o-phenylenediamine | p-nitro-o-phenylenediamine | >0.01 |
| HC Yellow No. 5 | HC Yellow No. 5 | >0.01 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 11

The constituents for Example 11 result in an orange colored clay pack for coloring and conditioning brunette hair. The constituents are the same a listed in Example 2, with the following variations:

| CTFA Designation | Trade Name | % by Weight |
| --- | --- | --- |
| Henna Extract | Henna Extract | 2.00 |
| o-nitro-p-phenylenediamine | o-nitro-p-phenylenediamine | 0.07 |
| Intersperse Pink B2 | Intersperse Pink B2 | 0.06 |
| HC Yellow No. 5 | HC Yellow No. 5 | 0.06 |
| HC Yellow No. 4 | HC Yellow No. 4 | 0.09 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 12

The constituents for Example 12 result in a red-orange colored clay pack for coloring and conditioning brunette hair. The constituents are the same as listed in Example 2, with the following variations:

| CTFA Designation | Trade Name | % by Weight |
| --- | --- | --- |
| Henna Extract | Henna Extract | 2.00 |
| HC Blue No. 1 | HC Blue No. 1 | 0.02 |
| o-nitro-p-phenylenediamine | o-nitro-p-phenylenediamine | 0.10 |
| HC Yellow No. 5 | HC Yellow No. 5 | 0.15 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Tetrasodium EDTA | Hampene 100 | 0.25 |
| Gluteral | Ucarcide 225 | 0.15 |
| DMDM Hydantoin | Glydant | 0.35 |

EXAMPLE 13

The constituents for Example 13 result in a mahogany colored clay pack for coloring and conditioning brown, dark brown or black hair. The constituents are the same as listed in Example 2, with the following variations:

| CTFA Designation | Trade Name | % by Weight |
| --- | --- | --- |
| HC Blue No. 2 | HC Blue No. 2 | 0.05 |
| o-nitro-p-phenylenediamine | o-nitro-p-phenylenediamine | 0.50 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Gluteral | Ucarcide 225 | 0.15 |
| DMDM Hydantoin | Glydant | 0.35 |

EXAMPLE 14

The constituents for Example 14 result in a bright red colored clay pack for coloring and conditioning golden blonde hair. The constituents are the same as listed in Example 2, with the following variations:

| CTFA Designation | Trade Name | % by Weight |
| --- | --- | --- |
| Intersperse Pink B2 | Intersperse Pink B2 | 0.40 |
| Dispersed Black No. 9 | Dispersed Black No. 9 | 0.30 |
| HC Yellow No. 4 | HC Yellow No. 4 | 0.10 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Gluteral | Ucarcide 225 | 0.15 |
| DMDM Hydantoin | Glydant | 0.35 |

EXAMPLE 15

The constituents for Example 15 result in a orange-brown colored clay pack for coloring and conditioning dark blonde, light brown and dark brown hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.15 |
| HC Blue No. 1 | HC Blue No. 1 | 0.02 |
| HC Yellow No. 4 | HC Yellow No. 4 | 0.18 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |
| Polymethoxy bicyclic Oxazolidine | Nuosept C | 0.00 |
| Gluteral | Ucarcide 225 | 0.15 |
| DMDM Hydantoin | Glydant | 0.35 |

EXAMPLE 16

The constituents for Example 16 result in a opaque deep burgundy colored clay pack for coloring and conditioning medium brown, dark brown, and black hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.50 |
| HC Blue No. 2 | HC Blue No. 2 | 0.05 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 17

The constituents for Example 17 result in a opaque deep burgundy colored clay pack for coloring and conditioning medium brown, dark brown, and black hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.63 |
| HC Blue No. 2 | HC Blue No. 2 | 0.06 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 18

The constituents for Example 18 result in a opaque deep burgundy colored clay pack for coloring and conditioning medium brown, dark brown, and black hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.75 |
| HC Blue No. 2 | HC Blue No. 2 | 0.08 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 19

The constituents for Example 19 result in an opaque deep burgundy colored clay pack for coloring and conditioning medium brown, dark brown, and black hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 1.50 |
| HC Blue No. 2 | HC Blue No. 2 | 0.15 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 20

The constituents for Example 10 result in a opaque brown colored clay pack for coloring and conditioning light brown, medium brown and dark brown hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.50 |
| HC Blue No. 2 | HC Blue No. 2 | 0.15 |
| p-nitro-o-phenylenediamine | p-nitro-o-phenylenediamine | 0.05 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 21

The constituents for Example 21 result in a brown colored clay pack for coloring and conditioning light brown, medium brown and dark brown hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.50 |
| HC Blue No. 2 | HC Blue No. 2 | 0.15 |
| p-nitro-o-phenylenediamine | p-nitro-o-phenylenediamine | 0.10 |
| Disperse Violet No. 1 | Disperse Violet No. 1 | 0.00 |
| D&C Violet No. 2 | D&C Violet No. 2 | 0.00 |
| External D&C Violet No. 2 | External D&C Violet No. 2 | 0.00 |

EXAMPLE 22

The constituents for Example 22 result in an opaque brownish-burgundy colored clay pack for coloring and conditioning light brown, medium brown and dark brown hair. The constituents are the same as listed in Example 2, with the following variations:

| CTFA Designation | Trade Name | % by Weight |
|---|---|---|
| o-nitro-p-phenylenediamine | o-nitro-p-phenylenediamine | 0.50 |
| HC Blue No. 2 | HC Blue No. 2 | 0.15 |
| Disperse Violet No. 1 | Disperse Violet No. 1 | 0.00 |

EXAMPLE 23

The constituents listed below result in a bright violet colored clay pack for coloring and conditioning white or grey hair.

| CTFA Designation | Trade Name | % by Weight |
|---|---|---|
| Deionized Water | Deionized Water | Q.S. to 100% |
| Henna Extract | Henna Extract | 2.00 |
| Methylparaben | Methylparaben | 0.30 |
| Magnesium Aluminum Silicate | Veegum HV | 1.00 |
| Sodium Hyaluronate | Lifecore Sodium Hyaluronate | >0.01 |
| Glycerin | Glycerin | 0.30 |
| Honey | Honey Blend #3 | 0.10 |
| Acetamide MEA | Acetamide MEA | 0.01 |
| Oat Flour | Stero Pro | 1.34 |
| PVM/MA Copolymer | Gantrez AN 169 (sol.) | 4.00 |
| Quaternium-22 | Ceraphyl 60 | 0.01 |
| Hydrolyzed Animal Protein | Lexein 250 | 6.00 |
| Cationic Collagen Polypeptides | Cationic Collagen Polypeptides (Amerchol) | 1.50 |
| Cocodimonium Hydrolyzed Animal Protein | Croquat M | 1.50 |
| Stearyl Alcohol | Stearyl Alcohol | 0.10 |
| Panthenol DL | Panthenol | 0.50 |
| Cetyl Alcohol | Cetyl Alcohol | 3.06 |
| Glyceryl Stearate (and) PEG-100 Stearate | Arlacel 165 | 1.64 |
| Cetearyl Alcohol (and) PEG-40 Castor Oil (and) Stearalkonium Chloride | Cycloton SCS | 1.00 |
| Cetearyl Alcohol (and) Polysorbate 60 (and) Stearalkonium Chloride | Mazerwax 163 | 1.80 |
| Dimethyl Lauramine Oleate | Necon Lo | 2.00 |
| Dicetyldimonium Chloride | Adogen 432 CG | 0.43 |
| Propylparaben | Propylparaben | 0.10 |
| PPG-5 Lanolin Ether | Solulan PB-5 | 0.16 |
| Disperse Violet No. 1 | Disperse Violet No. 1 | 0.03 |
| Cyclomethicone | Dow Corning 345 | 0.23 |
| Dimethicone | Dow Corning 200 | 0.23 |
| Tetrasodium EDTA | Hampene 100 | 0.50 |
| PEG-15 Tallow Polyamine | Polyquart H | 0.50 |
| DMDM Hydantoin | Glydant | 0.35 |
| Kaolin | Huber 35/Hydrite | 6.50 |
| Fullers Earth | Fullers Earth 100 | 2.70 |
| Amodimethicone (and) Nonoxynol-10 (and) Tallowtrimonium Chloride | Dow Corning 929 Emulsion | 3.00 |
| Nonoxynol-10 | Surfonic N-95 | 0.01 |
| Fragrance | Fragrance | Q.S. |

-continued

| CTFA Designation | Trade Name | % by Weight |
|---|---|---|
| D&C Violet No. 2 | D&C Violet No. 2 | 0.00 |
| External D&C Violet No. 2 | External D&C Violet No. 2 | 0.00 |

While the above example has been described with particularity, it is to be understood that the dye loads incorporated into the clay-based compositions of the present invention can occur at anywhere between about 0.00001 to 5.00 percent by weight, depending upon the tone and intensity of coloration sought. In addition, the other listed components can occur within any range of values which render effective clay-based coloring and conditioning compositions in accordance with the present invention. For example, the water component can occur at anywhere between about 20-70% by weight, the clay components between about 5-25% by weight, the moisturizing components between about 0.10-5.00% by weight, the henna component between about 1-15% by weight, the protein components between about 2-20% by weight, the sodium hyaluronate between about 0.00001-1.00% by weight and the emulsifying components between about 0.25-10.00% by weight.

EXAMPLE 24

The constituents for Example 24 result in a golden wheat colored clay pack for coloring and conditioning blonde hair. The constituents are the same as listed in Example 23, with the following variations:

| CTFA Designation | Trade Name | % by Weight |
|---|---|---|
| Intersperse Pink B2 | Intersperse Pink B2 | 0.07 |
| HC Black No. 9 | HC Black No. 9 | 0.10 |
| Disperse Violet No. 1 | Disperse Violet No. 1 | 0.00 |

EXAMPLE 25

The constituents for Example 25 result in a navy blue colored clay pack for coloring and conditioning brunette hair. The constituents are the same as listed in Example 23, with the following variations:

| CTFA Designation | Trade Name | % by Weight |
|---|---|---|
| HC Blue No. 1 | HC Blue No. 1 | 0.16 |
| HC Blue No. 2 | HC Blue No. 2 | 0.19 |
| Disperse Violet No. 1 | Disperse Violet No. 1 | 0.00 |

EXAMPLE 26

The constituents for Example 26 in an orange colored clay pack for coloring and conditioning brunette hair. The constituents are the same as listed in Example 23, with the following variations:

| CTFA Designation | Trade Name | % by Weight |
|---|---|---|
| o-nitro-p-phenylenediamine | o-nitro-p-phenylenediamine | 0.07 |
| Intersperse Pink B2 | Intersperse Pink B2 | 0.06 |
| HC Yellow No. 4 | HC Yellow No. 4 | 0.09 |
| HC Yellow No. 5 | HC Yellow No. 5 | 0.06 |
| Disperse Violet No. 1 | Disperse Violet No. 1 | 0.00 |

It is to be understood, however, that even though numerous characteristics and advantages of the invention have been set forth in the foregoing description, the disclosure is illustrative only, and changes may be made in detail within the principle of the invention, to the full extent indicated by the broad general meaning of the terms in which the appended claims are expressed.

What is claimed is:

1. A composition for coloring hair comprising: about 20-70% water;
   about 5-25% clay;
   0.00001-5.0% of a coloring component, wherein said coloring component is selected from the group consisting of a non-permanent coloring agent and a semi-permanent coloring agent;
   about 0.1-5.0% moisturizer component;
   about 2-20% reconstruction component; and
   about 0.5-20% shine imparting component or any combination thereof.

2. A composition of claim 1 wherein the combination is:
   about 2–20% reconstruction component;
   about 0.1–5.0% moisturizer component; and
   about 0.5–20% shine imparting component.

3. A composition of claim 1 wherein the coloring component is a non-permanent coloring agent selected from the group consisting of FD&C colors and dyes, D&C colors and dyes, H&C colors and dyes and oxidation dye intermediates.

4. A composition of claim 1 wherein the coloring component is a semi-permanent coloring agent selected from the group consisting of pyrazolone compounds, monoazo compounds, xanthene compounds, triphenylmethane compounds, diazo compounds, metal-complex dyes and oxidation dye intermediates.

5. A composition of claim 4 wherein the semi-permanent coloring agent is a metal-complex dye selected from the group consisting of cobalt azo complexes and chromium azo complexes.

6. A composition of claim 4 wherein the oxidation dye intermediation is a nitrophenylenediamine.

7. A composition of claim 6 wherein the nitrophenylenediamine is selected from the group consisting of o-nitro-p-phenylenediamine and p-nitro-o-phenylenediamine.

8. A composition of claim 1 wherein said reconstruction component is protein.

9. A composition of claim 1 wherein said moisturizer component comprises sodium hyaluronate.

10. A composition of claim 9 wherein the sodium hyaluronate is from about 0.00001–1.0% of said composition.

11. A composition of claim 1 wherein said shine imparting component comprises henna.

12. A composition of claim 11 wherein said henna is from about 1–15% of said composition.

13. A composition of claim 1 further comprising from about 0.25–10% of an emulsifier component.

14. A composition of claim 13 wherein said emulsifier component comprises a nonionic emulsifier and a cationic emulsifier.

15. A composition of claim 1 wherein said clay comprises kaolin and fuller's earth.

16. A composition of claim 15 wherein said kaolin is from about 2–12% of said composition and said fuller's earth is from about 0.5–7% of said composition.

17. A composition of claim 1 wherein said moisturizing component is from about 0.1–5% of said composition.

18. A composition of claim 1 further comprising about 2–10% of a fatty alcohol component.

19. A method for coloring hair comprising the steps of:
   (a) applying to hair an aqueous clay-based composition of about 20–70% water, about 5–25% clay, about 0.00001–5.0% of a coloring component, wherein said coloring component is selected from the group consisting of a non-permanent coloring agent and a semi-permanent coloring agent, and a hair conditioning component comprised of about 0.1–5.0% of a moisturizer component, about 2–20% of a reconstruction component, about 0.5–20% of a shine imparting component or any combination thereof; and
   (b) exposing the hair to heat for a period of time between about 15–45 minutes at a temperature of from about 80°–120° F.

20. A method for coloring hair comprising the steps of:
   (a) applying an aqueous based paste of about 20–70% water, about 5–25% clay about 0.00001–5.0% of a coloring component to hair on an individual'head, wherein said coloring component is selected from the group consisting of a non-permanent coloring agent and a semi-permanent coloring agent;
   (b) enclosing the hair in cover means;
   and a hair conditioning component comprised of about 0.1–5.0% of a moisturizer component, about 2–20% of a reconstruction component, about 0.5–20% of a shine imparting component or any combination thereof;
   (c) exposing the hair to a temperature of from about 80°–120° F. for a period of time between about 15–45 minutes;
   (d) removing the cover means; and
   (e) exposing the hair to a temperature of from about 80°–120° F. for a period of time between about 2–15 minutes.

21. A method according to claim 20 wherein the hair in step (c) is exposed to a temperature of from about 90°–110° F. for a period of time between about 20–30 minutes and the hair in step (e) is exposed to a temperature of from about 90°–110° F. for a period of time between 3–8 minutes.

22. A method according to claim 20 wherein said clay is a mixture of kaolin and fuller's earth.

23. A method according to claim 20 wherein the coloring component is a non-permanent coloring agent selected from the group consisting of FD&C colors and dyes, D&C colors and dyes, H&C colors and dyes and oxidation dye intermediates.

24. A method according to claim 20 wherein the coloring component is a semi-permanent coloring agent selected from the group consisting of pyrazolone compounds, monoazo compounds, xanthene compounds, triphenylmethane compounds, diazo compounds, metal-complex dyes and oxidation dye intermediates.

25. A method according to claim 24 wherein the semi-permanent coloring agent is a metal-complex dye selected from the group consisting of cobalt azo complexes and chromium azo complexes.

26. A method according to claim 24 wherein the oxidation intermediate is a nitrophenylenediamine.

27. A method according to claim 26 wherein the nitrophenylenediamine is selected from the group consisting of o-nitro-p-phenylenediamine and p-nitro-o-phenylenediamine.

28. A method a claim 20 wherein said reconstruction component is protein.

29. A method according to claim 20 wherein said moisturizer component comprises sodium hyaluronate.

30. A method according to claim 29 wherein the sodium hyaluronate is from about 0.000001–1.0% of said composition.

31. A method according to claim 20 wherein said shine imparting component comprises henna.

32. A method according to claim 31 wherein said henna is from about 1–15% of said composition.

33. A method according to claim 20 further comprising from about 0.25–10% of an emulsifier component.

34. A method according to claim 33 wherein said emulsifier component comprises a nonionic emulsifier and a cationic emulsifier.

* * * * *